United States Patent [19]

Delaney et al.

[11] Patent Number: 4,552,866
[45] Date of Patent: Nov. 12, 1985

[54] USE OF DIAMINO ALCOHOLS AS ANALGESIC AGENTS

[75] Inventors: Norma G. Delaney, Princeton; Eric M. Gordon, Pennington, both of N.J.

[73] Assignee: E. R. Squibb & Sons, Inc., Princeton, N.J.

[21] Appl. No.: 628,004

[22] Filed: Jul. 5, 1984

[51] Int. Cl.[4] .................. A61K 37/00; C07C 103/52
[52] U.S. Cl. ........................................ 514/16; 514/17; 514/18; 514/19; 260/112.5 R
[58] Field of Search ............... 514/16, 17, 18, 19; 260/112.5 R

[56] References Cited

FOREIGN PATENT DOCUMENTS 0104041 9/1983 European Pat. Off. ...... 260/112.5 R

OTHER PUBLICATIONS

H. Umezawa et al., J. Antibiotics, vol. 29, p. 97, (1976).
H. Suda et al., J. Antibiotics, vol. 29, p. 100, (1976).
T. Aoyagi et al., J. Antibiotics, vol. 31, p. 636, (1978).
H. Tobe et al., Agric. Biological Chemistry, vol. 43, p. 591, (1979).
Inhibition of Brain Aminopeptidase by Bestatin and Analogs, G. W. Wagner & J. E. Dixon, J. Neurochem. vol. 37, p. 709, (1980).

Primary Examiner—Delbert R. Phillips
Attorney, Agent, or Firm—Lawrence S. Levinson; Donald J. Barrack

[57] ABSTRACT

An enkephalin-degrading aminopeptidase enzyme is inhibited by compounds having the formula

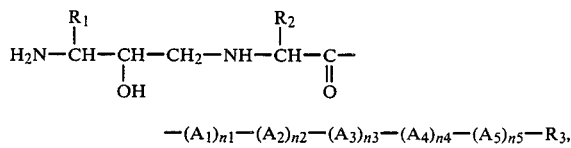

$$-(A_1)_{n1}-(A_2)_{n2}-(A_3)_{n3}-(A_4)_{n4}-(A_5)_{n5}-R_3,$$

and pharmaceutically acceptable salt thereof, wherein $R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

$R_3$ is hydroxy, alkoxy, (substituted alkyl)oxy, arylalkoxy, (heteroaryl)alkoxy or $-NY_1Y_2$, wherein $Y_1$ and $Y_2$ are each independently hydrogen, alkyl, aryl, or arylalkyl or $Y_1$ is hydrogen and $Y_2$ is substituted alkyl or (heteroaryl)alkyl;

$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

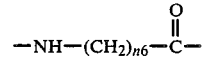

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, or prolyl, norleucyl, or norvalyl; and $n_1$, $n_2$, $n_3$, $n_4$ and $n_5$ each is independently 0 or 1.

15 Claims, No Drawings

USE OF DIAMINO ALCOHOLS AS ANALGESIC AGENTS

RELATED APPLICATION

U.S. patent application Ser. No. 515,729, filed July 21, 1983, now U.S. Pat. No. 4,514,391, discloses angiotensin converting enzyme inhibitors (hypotensive agents) having the formula

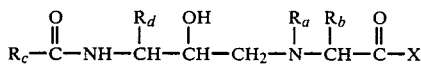

wherein X is an amino (or imino) acid residue, $R_a$ is hydrogen, alkyl, cycloalkyl, or specified substituted alkyl groups; $R_b$ is hydrogen, alkyl, or specified substituted alkyl groups; $R_c$ is specified substituted alkyl groups; and $R_d$ is hydrogen, alkyl or specified substituted alkyl groups.

BRIEF DESCRIPTION OF THE INVENTION

Compounds having the formula

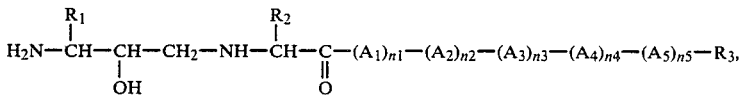

and pharmaceutically acceptable salts thereof, possess inhibitory activity against an enkephalin-degrading aminopeptidase, and can be used as analgesic agents alone, or in conjunction with an enkephalinase inhibitor. This invention is directed to the treatment of pain in a mammalian host by the administration of a compound of formula I. Those compounds of formula I having the formula

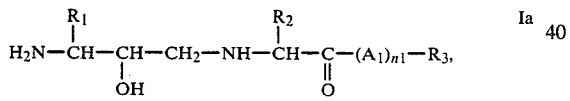

and pharmaceutically acceptable salts thereof, are novel, and as such, form an integral part of this invention.

In formulas I and Ia, and throughout the specification, the symbols are as defined below.

$R_1$ and $R_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

$R_3$ is hydroxy, alkoxy, (substituted alkyl)oxy, arylalkoxy, (heteroaryl)alkoxy, or $-NY_1Y_2$, wherein $Y_1$ and $Y_2$ are each independently hydrogen, alkyl, aryl, or arylalkyl, or $Y_1$ is hydrogen and $Y_2$ is substituted alkyl or (heteroaryl)alkyl;

$A_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

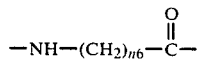

wherein $n_6$ is an integer of 2 to 15;

$A_2$, $A_3$, $A_4$ and $A_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and $n_1, n_2, n_3, n_4$ and $n_5$ each is independently 0 or 1.

The terms "alkyl" and "alkoxy", as used throughout the specification either individually or as part of a larger group, refer to straight and branched chain groups having 1 to 7 carbon atoms.

The term "halo substituted alkyl", as used throughout the specification either individually or as part of a larger group, refers to alkyl groups in which one, or more, hydrogens have been replaced by chloro, bromo or fluoro groups. Exemplary groups are trifluoromethyl, which is preferred, pentafluoroethyl, 2,2,2-trichloroethyl, chloromethyl and bromomethyl.

The term "cycloalkyl", as used throughout the specification either individually or as part of a larger group, refers to cycloalkyl groups having 3, 4, 5, 6 or 7 carbon atoms.

The term "substituted alkyl", as used throughout the specification, either individually or as part of a larger group, refers to alkyl groups substituted with one, or more (preferably one), hydroxy or $-NY_3Y_4$ groups, wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

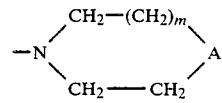

and A is CH—Q, oxygen, or N—Q, Q is hydrogen or alkyl and m is 0 or 1.

The term "heteroaryl", as used throughout the specification either individually or as part of a larger group, refers to 2- or 3-furanyl, 2- or 3-thienyl, 2-, 3- or 4-pyridinyl, 4-imidazolyl and 3-indolyl.

The term "aryl", as used throughout the specification either individually or as part of a larger group, refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

DETAILED DESCRIPTION OF THE INVENTION

The compounds of formula I, and the pharmaceutically acceptable salts thereof, can be administered to a mammalian specie as an analgesic agent due to their ability to inhibit an enkephalin-degrading aminopeptidase.

It is well known that the weak and short-lasting analgesic activity of endogenous enkephalins can be attributed to their rapid inactivation. Enkephalins are metabolized by several hydrolytic enzymes present in the brain: (1) aminopeptidases release the Tyr[1] residue, (2) a dipeptidyl aminopeptidase releases the $Tyr^1$-$Gly^2$ residue and (3) two enzymes cleave the penultimate $Gly^3$-$Phe^4$ bond to release an intact dipeptide fragment, angiotensin-converting enzyme, and a discrete enzyme commonly designated enkephalinase.

It has been suggested that both enkephalinase and an aminopeptidase activity (probably membrane-bound) play key roles in enkephalin metabolism. The compounds of this invention inhibit the aminopeptidase activity and thus act as analgesic agents.

A compound of formula I, or a pharmaceutically acceptable salt thereof, can be administered to patients orally or parenterally in an effective amount within the daily dosage range of about 0.1 to about 25 milligrams of compound per kilogram of patient body weight. Administration can be once daily or in 2 to 4 divided daily doses.

Those compounds of formula I, and pharmaceutically acceptable salts thereof, wherein $R_2$ is a lipophilic side-

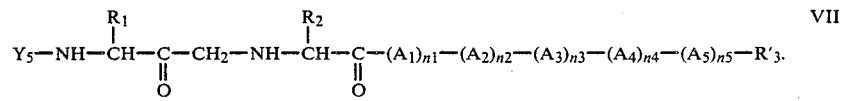

chain, especially arylalkyl (e.g., benzyl) exhibit inhibitory activity against enkephalin cleaving endopeptidase in addition to the above-described aminopeptidase activity.

The compounds used in the method of this invention can be prepared utilizing as a starting material an amino acid having the formula

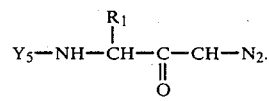

The amino group is first protected using, for example, a classical protecting group such as t-butyloxycarbonyl, benzyloxycarbonyl, or o-nitrophenylsulfenyl, and yielding a compound having the formula

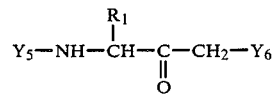    III wherein $Y_5$ is a nitrogen protecting group.

An activated form of an acid of formula III (preferably a mixed anhydride) can be reacted with diazomethane to yield the corresponding diazo compound having the formula $$Y_5-NH-CH(R_1)-C(=O)-CH-N_2.$$   IV Reaction of a compound of formula IV with hydrogen chloride or hydrogen bromide yields the corresponding compound having the formula $$Y_5-NH-CH(R_1)-C(=O)-CH_2-Y_6$$   V wherein $Y_6$ is chlorine or bromine.

Reaction of a compound of formula V with an amino acid or peptide having the formula

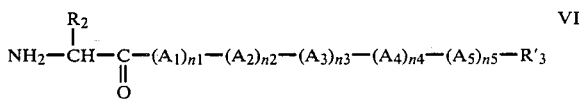    VI yields the corresponding compound

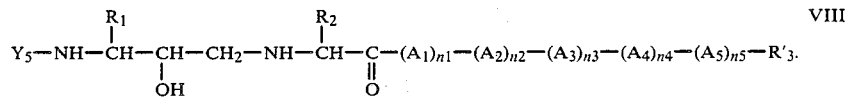    VII

In formulas VI and VII, and throughout the specification, the symbol $R'_3$ is alkoxy, (substituted alkyl)oxy, arylalkoxy, (heteroaryl)alkoxy or $-NY_1Y_2$. The reaction is preferably carried out in the presence of a base such as sodium bicarbonate.

Reduction of a compound of formula VII with a chemical reducing agent such as sodium borohydride, which is preferred, sodium cyanoborohydride, or a lithium trialkyl aluminum hydride, yields the corresponding compound having the formula

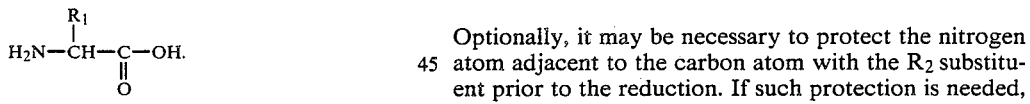    VIII

Optionally, it may be necessary to protect the nitrogen atom adjacent to the carbon atom with the $R_2$ substituent prior to the reduction. If such protection is needed, conventional techniques can be used to add a protecting group to the compound of formula VII and remove it after the reduction is completed.

The products of formula I are obtained from the corresponding compounds of formula VIII using standard deprotection techniques. The particular deprotection reaction used will, of course, depend on the particular $Y_5$ protecting group present.

Alternatively, the compounds of formula I can be prepared by first synthesizing a halomethyl ketone of formula V and then reducing it to the corresponding alcohol having the formula

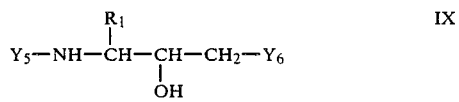    IX with a chemical reducing agent.

Treatment of a compound of formula IX with sodium hydride in a solvent such as tetrahydrofuran yields the corresponding oxirane compound having the formula

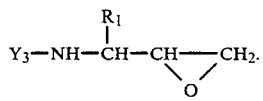

Reaction of a compound of formula X with an amino acid or peptide of formula VI under reflux conditions (alcohol is the preferred solvent) yields the intermediate of formula VIII, which can be treated as described above to yield the desired products of formula I.

The compounds of formula I wherein $R_3$ is hydroxy form basic salts with a variety of inorganic and organic bases. The pharmaceutically acceptable salts include alkali metal salts such as sodium or potassium, alkaline earth metal salts such as calcium or magnesium, and salts derived from amino acids such as arginine, lysine, etc. The salts can be prepared by reacting the acid form of the compound, i.e., $R_3$ is hydroxy, with an equivalent of the base supplying the desired basic ion in a medium in which the salt precipitates or in aqueous medium and then lyophilizing.

Additionally, the compounds of formula I form acid-addition salts with a variety of inorganic and organic acids. The pharmaceutically acceptable salts include, for example, the hydrohalides, e.g., hydrochloride, hydrobromide, etc., sulfate, phosphate, nitrate, arylsulfonates, (e.g., camphorsulfonate, benzenesulfonate, toluene-sulfonate, etc.), citrate, ascorbate, maleate, fumarate, pamoate, acetate, tartrate, salicylate and the like. It is frequently convenient to isolate the compound by forming the acid salt and precipitating in a medium in which it is insoluble.

Products of formula I have one, or more, asymmetric carbon atoms. The carbon atom attached to the hydroxyl group is asymmetric, and if $R_1$ or $R_2$ is other than hydrogen, the carbon atom to which it is attached will also be asymmetric. The compounds, therefore, exist in stereoisomeric forms, and as racemic mixtures thereof. All of these are within the scope of this invention. The above-described syntheses can utilize the racemate or one of the diastereomers as the starting material. When the racemic starting material is used in the synthetic procedure, the stereoisomers obtained in the product can be separated by conventional chromatographic or fractional crystallization techniques. The amino acids designated $A_1$, $A_2$, $A_3$, $A_4$ and $A_5$ may be in the L or D configuration.

The following examples are specific embodiments of this invention. Additionally, they provide alternative processes for preparing the compounds of this invention.

EXAMPLE 1

N-[N-[(3S)-3-Amino-2-hydroxybutyl]-L-phenylalanyl]-L-leucine, dihydrochloride (faster isomer)

(A) [(S)-3-Diazo-1-methyl-2-oxopropyl]carbamic acid, 1,1-dimethylethyl ester

To a vigorously stirred solution of [(t-butyloxy)carbonyl]-L-alanine (15.14 g, 80 mmol) and N-methylmorpholine (8.80 ml, 80 mmol) in 80 ml of dry tetrahydrofuran at −15° C. under argon was added a solution of isobutyl chloroformate (10.37 ml, 80 mmol) in 10 ml tetrahydrofuran, maintaining the reaction temperature below −12° C. After the addition was complete, the reaction mixture was stirred for 14 minutes and then diluted with 250 ml of anhydrous ether (prechilled to −20° C.) and quickly filtered. Approximately one-fourth of the filtrate was transferred to a separatory funnel (the remainder kept chilled) and added rapidly to a gently stirred, chilled (0° C.) solution of diazomethane (160 mmol, generated from 23.54 g of N-methyl-N′-nitro-N-nitrosoguanidine). Additional chilled portions were transferred to the separatory funnel until the entire solution had been added (over approximately 10 minutes). The resulting solution was stirred for 2 hours, warming gradually to room temperature, then purged with nitrogen for 1 hour, washed with chilled half-saturated sodium bicarbonate (2×100 ml) and water (3×50 ml), dried (sodium sulfate) and evaporated to a yellow semi-crystalline residue. Two recrystallizations from ethyl acetate-petroleum ether yielded yellow plates, 10.29 g, melting point 99°–102° C., plus an additional crop of 1.33 g, melting point 97.5°–101° C. A portion was recrystallized once more giving the analytical sample, melting point 102°–103° C.

(B) [(S)-3-Chloro-1-methyl-2-oxopropyl]carbamic acid, 1,1-dimethylethyl ester

Hydrogen chloride gas was slowly bubbled into a chilled (0°–5° C.) solution of [(S)-3-diazo-1-methyl-2-oxopropyl]carbamic acid, 1,1-dimethylethyl ester (9.58 g, 44.9 mmol) in 400 ml of ether until the solution was colorless and nitrogen evolution ceased. The solution was refrigerated for 1 hour, then washed with ice-water (3×50 ml), dried (sodium sulfate) and evaporated yielding 9.87 g of a white crystalline solid, melting point 64°–66.5° C. A portion was recrystallized from ether-petroleum ether giving the analytical sample, melting point 65.5°–67° C.

(C) N-[N-[(S)-3-[[(t-Butyloxy)carbonyl]amino]-2-oxobutyl]-L-phenylalanyl]-L-leucine, t-butyl ester To a stirred solution of L-phenylalanyl-L-leucine, t-butyl ester (2.18 g, 6 mmol) in 10 ml of dimethylformamide (under argon) was added a solution of [(S)-3-chloro-1-methyl-2-oxopropyl]carbamic acid, 1,1-dimethylethyl ester (1.33 g, 6 mmol) in 20 ml of dimethylformamide, followed by sodium iodide (450 mg, 3 mmol) and sodium bicarbonate (504 mg, 6 mmol). The reaction mixture was allowed to stir for 15 hours, then the solvent was evaporated (<25C° C., vacuum pump). The yellow residue was taken up into ethyl acetate (250 ml) and washed with water (4×25 ml) and brine (25 ml), then dried (sodium sulfate) and evaporated to a yellow residue (3.44 g). Flash chromatography on silica gel (Merck, 230–400 mesh, 250 g) with hexane-ethyl acetate (1.25:1) yielded 2.29 g of a colorless oil. Rapid recrystallization from ethyl acetate-hexane afforded 1.61 g of a powdery white solid.

(D) N-[N-[(3S)-3-[[(t-Butyloxy)carbonyl]amino]-2-hydroxybutyl]-L-phenylalanyl]-L-leucine, t-butyl ester To a solution of N-[N-[(S)-3-[[(t-butyloxy)carbonyl]amino]-2-oxobutyl]-L-phenylalanyl]-L-leucine, t-butyl ester (1.50 g, 2.89 mmol) in 15 ml of methanol at 0° C. was added sodium borohydride (109 mg, 2.89 mmol) in six portions over approximately 5 minutes. After 15 minutes, the solvent was evaporated. The residue was taken up into ethyl acetate (100 ml), washed with water until the extracts were neutral, washed with brine and then dried (sodium sulfate) and evaporated to give 1.41 g of the title compound as a mixture of diastereomers.

(E)
N-[N-[(3S)-3-[[(t-Butyloxy)carbonyl]amino]-2-hydroxybutyl]-L-phenylalanyl-L-leucine, t-butyl ester (faster isomer)

The mixture of aminoalcohols prepared above (1.41 g) was applied to a column of silica gel (Merck, 230–400 mesh, 200 g) and flash chromatographed with hexane-ethyl acetate (1:1). Fractions 50–79 (~15 ml each) were pooled and concentrated yielding 0.76 g of the faster eluting isomer, (TLC, $R_f$=0.42, ethyl acetate-petroleum ether (2:1)).

(F)
N-[N-[(3S)-3-Amino-2-hydroxybutyl]-L-phenylalanyl]-L-leucine, dihydrochloride (faster isomer)

To a solution of N-[N-[(3S)-3-[[(t-butyloxy)carbonyl]amino]-2-hydroxybutyl]-L-phenylalanyl-L-leucine, t-butyl ester (faster isomer) (0.33 g, 0.64 mmol) in 3.5 ml of dichloromethane was added trifluoroacetic acid (2 ml). The resulting solution was stoppered and allowed to stand for 1 hour at room temperature, and the solvent was then evaporated. Analysis of the residue by $^{13}$C-NMR showed a considerable amount of unreacted t-butyl ester. The recovered material was treated with 10 ml of ~1.5N hydrogen chloride in acetic acid for 1.5 hours at room temperature. The solvent was evaporated (<25° C., vacuum pump) and the residue was triturated with ether yielding a white solid. Analysis by $^{13}$C-NMR again revealed t-butyl resonances, although diminished in intensity. The aforementioned hydrogen chloride/acetic acid treatment was repeated three more times, finally yielding 200 mg of the title compound as a white solid, melting point 174°–177° C. (changes form 127°–131° C.).

Analysis Calc'd. for $C_{19}H_{31}N_3O_4 \cdot 2HCl \cdot 1.5H_2O$: C, 49.03; H, 7.80; N, 9.03; Cl, 15.23. Found: C, 48.97; H, 7.55; N, 9.08; Cl, 14.93.

EXAMPLE 2

N-[N-[(3S)-3-Amino-2-hydroxybutyl]-L-phenylalanyl]-L-leucine, dihydrochloride (slower isomer)

(A)
N-[N-[(3S)-3-[[(t-Butyloxy)carbonyl]amino]-2-hydroxybutyl]-L-phenylalanyl-L-leucine, t-butyl ester (slower isomer)

A mixture of diastereomers of N-[N-[(3S)-3-[[(t-butyloxy)carbonyl]amino]-2-hydroxybutyl]-L-phenylalanyl-L-leucine, t-butyl ester (1.41 g) was prepared and chromatographed as described in example 1E. Fractions 80–116 (~15 ml each) were pooled and concentrated yielding 0.39 g of a mixture of isomers. Fractions 117–180 were combined and concentrated yielding 0.15 g of the slower isomer, contaminated with a small amount of the faster isomer. The material from the overlap fractions (80–116) was reapplied to the same column and eluted with hexane-ethyl acetate (1:1) yielding an additional 0.12 g of material comparable in composition to the material from fractions 117–180. These samples were combined yielding 0.27 g of the slower isomer, contaminated with a small amount of the faster isomer (TLC, $R_f$=0.31, ethyl acetate-petroleum ether (2:1)).

(B)
N-[N-[(3S)-3-Amino-2-hydroxybutyl]-L-phenylalanyl]-L-leucine, dihydrochloride (slower isomer)

A solution of N-[N-[(3S)-3-[[(t-butyloxy)carbonyl]amino]-2-hydroxybutyl]-L-phenylalanyl-L-leucine, t-butyl ester (slower isomer) (0.27 g, 0.52 mmol) in 20 ml of 1.3N hydrogen chloride in acetic acid was allowed to stir for 2 hours at room temperature, during which time a white precipitate separated. The mixture was concentrated under reduced pressure to approximately one third of the original volume, then diluted with ether and filtered yielding 185 mg of the title compound as a white solid, melting point 236°–239° C. (with slow decomposition >210° C.). Analysis by 400 MHz $^1$H-NMR revealed the presence of a small amount (<5%) of the faster isomer.

Analysis Calc'd. for $C_{19}H_{31}N_3O_4 \cdot 2HCl \cdot 1.0H_2O$: C, 50.00; H, 7.73; N, 9.21; Cl, 15.54 Found: C, 49.88; H, 7.48; N, 8.97; Cl, 15.76

EXAMPLE 3

N-[(3S)-3-Amino-2-hydroxy-4-phenylbutyl]-L-phenylalanine, dihydrochloride (A) [(Phenylmethoxy)carbonyl]-L-phenylalanine chloromethyl ketone To a stirred solution (at -15° C.) of [(phenylmethoxy)carbonyl-L-phenylalanine (20 g, 66.8 mmol) and N-methylmorpholine (7.4 ml, 66.8 mmol) in tetrahydrofuran (60 ml) was added isobutylchloroformate (8.7 ml, 66.8 mmol) in drops, maintaining the reaction temperature at −15° C. After stirring for twelve minutes the mixture was filtered. The filtrate, after diluting with ice cold ether (300 ml), was added in drops to a stirred (ice bath) solution of ethereal diazomethane (generated from 30 g of N-methyl-N'-nitro-N-nitrosoguanidine). The reaction mixture was stirred at room temperature for two hours. A stream of argon was blown over the solution to remove excess diazomethane. The ethereal solution was washed with water, saturated sodium bicarbonate and saturated sodium chloride solutions. After removing ether, the crude product was crystallized from ethyl acetate-hexane to afford [(phenylmethoxy)carbonyl]-L-phenylalanine diazoketone (18.1 g), melting point 89°–90° C., $[\alpha]_D^{22}$ −55.1° (c 1.6, dimethylformamide).

The above diazoketone (12 g, 37.1 mmol) was suspended in ether (400 ml) and hydrogen chloride gas was bubbled through the solution for 20 minutes; it became a homogeneous solution. After concentrating in vacuo, the crude product was triturated with hexane to afford [(phenylmethoxy)carbonyl]-L-phenylalanine chloromethyl ketone (12.3 g), melting point 107°–108° C., $[\alpha]_D^{22}$= +30.0° (c=2.4, chloroform).

(B)
N-[(3S)-3-[[(Phenylmethoxy)carbonyl]amino]-2-oxo-4-phenylbutyl]-L-phenylalanine, phenylmethyl ester, hydrochloride To a stirred solution of L-phenylalanine, phenylmethyl ester (1.85 g, 7 mmol) in 35 ml of dimethylformamide (under argon) was added [(phenylmethoxy)carbonyl]-L-phenylalanine chloromethyl ketone (2.32 g, 7 mmol), sodium bicarbonate (588 mg, 7 mmol) and sodium iodide (525 mg, 3.5 mmol). The reaction mixture was allowed to stir for 15 hours, then the solvent was evaporated (<25° C., vacuum pump). The residue was taken up into ethyl acetate (150 ml) and washed with water (3×30 ml) and brine (1×20 ml), then dried (sodium sulfate) and evaporated to give a yellow gum (4.23 g). This material was applied to a column of silica gel (Merck, 230–400 mesh, 325 g) and flash chromatographed with hexane-ethyl acetate (2.5:1) to give 3.14 g of a slightly yellow oil.

A 1.98 g (3.6 mmol) portion of this oil was dissolved in 50 ml of 95% ethanol, cooled to 0°–5° C. and then treated with 7.2 ml (2 equiv.) of 1N hydrogen chloride. Approximately 5 ml of water was added, and the crystals which separated were collected to give 1.52 g of a white solid. Evaporation of the mother liquor gave 0.38 g of a slightly yellow solid. These samples were combined with 0.22 g of hydrochloride salt similarly prepared to yield 2.12 g of hydrochloride salt.

(C)
N-[(3S)-3-[[(Phenylmethoxy)carbonyl]amino]-2-hydroxy-4-phenylbutyl]-L-phenylalanine, phenylmethyl ester A solution of N-[(3S)-3-[[(phenylmethoxy)carbonyl]amino]-2-oxo-4-phenylbutyl]-L-phenylalanine, phenylmethyl ester, hydrochloride (2.12 g, 3.6 mmol) in 72 ml of 3:1 tetrahydrofuran-water was cooled to 0° C. Sodium borohydride (681 mg, 18 mmol) was added in approximately seven portions over 5–10 minutes. The reaction mixture was allowed to stir an additional 5 minutes and then poured into 150 ml of water. This mixture was extracted with 300 ml of ethyl acetate-ether (5:3). The organic extract was washed with water (2×50 ml) and brine (50 ml) and then dried (sodium sulfate) and evaporated to give 1.93 g of a colorless oil. This material was purified by flash chromatography on 150 g of Merck silica gel (230–400 mesh), eluting with hexane-ethyl acetate (1.25:1), to afford 1.14 g of the title compound as a white solid. The $^{13}$C-NMR spectrum was consistent with an approximately 2:1 mixture of alcohol diastereomers.

(D)
N-[(3S)-3-Amino-2-hydroxy-4-phenylbutyl]-L-phenylalanine, dihydrochloride

To a solution of N-[(3S)-3-[[(Phenylmethoxy)carbonyl]amino]-2-hydroxy-4-phenylbutyl]-L-phenylalanine, phenylmethyl ester (1.14 g, 2.06 mmol) in 30 ml of 95% ethanol was added 4.2 ml of 1N hydrogen chloride and 250 mg of 10% palladium on carbon catalyst. The reaction mixture was stirred at room temperature under an atmosphere of hydrogen. A white precipitate which separated upon addition of the aqueous hydrogen chloride redissolved as the reaction proceeded. After 17 hours, the catalyst was filtered and the solvent was evaporated. Trituration with methanol-ether afforded 531 mg of the title compound as a white solid, melting point 147°–163° C. The $^1$H-NMR showed an approximately 1:1 mixture of alcohol isomers. Evaporation of the filtrate from the trituration gave 0.21 g of material which was enriched in one of the diastereomers.

Analysis Calc'd. for $C_{19}H_{24}N_2O_3.2HCl$: C, 56.86; H, 6.53; N, 6.98; Cl, 17.67 Found: C, 56.94; H, 6.73; N, 6.73; Cl, 17.47

EXAMPLE 4
(3S)-1-[N-(3-Amino-2-hydroxy-4-phenylbutyl)-L-alanyl]-L-proline, trifluoroacetate salt (1:2)

(A) N-[(t-Butyloxy)carbonyl]-L-phenylalanine chloromethyl ketone

To a stirred solution of N-[(t-butyloxy)carbonyl]-L-phenylalanine (26.5 g, 100 mmol) in tetrahydrofuran (150 ml) at −20° C. was added isobutylchloroformate (13 ml, 100 mmol). N-Methylmorpholine (11 ml, 100 mmol) was then added in drops. The solution was stirred between −15° C. and −20° C. for fifteen minutes and then filtered. Tetrahydrofuran (25 ml) was used for the washings. The filtrate was added to a cold (ice bath) ethereal solution of diazomethane in drops. After the addition was over, the ice bath was removed, and the reaction mixture was stirred at ambient temperature for 2 hours. Nitrogen was blown over the solution and the volume was reduced to 400 ml. The reaction mixture was then stirred in an ice bath and hydrogen chloride in acetic acid (2N, 55 ml) was added in drops. After the addition was over, the ice bath was removed and the reaction mixture stirred for 15 minutes at room temperature. The reaction mixture was evaporated in vacuo and the residue on attempted dissolution in ether afforded 6.2 g of the title compound, melting point 104°–105° C.; $[\alpha]_D^{22} = +20.3°$ (c=2, chloroform). The mother liquor on concentration and after crystallization from ether/hexane afforded an additional 17.65 g of the title compound.

(B)
(3S)-1-[N-[3-[(t-Butyloxy)carbonyl]amino]-2-oxo-4-phenylbutyl-N-[(phenylmethoxy)carbonyl]-L-alanyl]-L-proline, t-butyl ester A solution of L-alanyl-L-proline t-butyl ester (1.0 g, 4.13 mmol), N-[(t-butyloxy)carbonyl]-L-phenylalanine chloromethyl ketone (1.2 g, 4.03 mmol), sodium bicarbonate (370 mg, 4.4 mmol) and sodium iodide (300 mg, 2 mmol) in dimethylformamide (7 ml) was stirred overnight at room temperature. The reaction mixture was evaporated. Dioxane (6 ml) was added to the residue followed by benzyloxycarbonyl chloride (0.75 ml, 5.24 mmol) and sodium bicarbonate (500 mg, 5.95 mmol). After stirring overnight, the reaction mixture was evaporated, the residue taken up in ethyl acetate and washed neutral (water, saturated sodium bicarbonate solution, water, 10% potassium bisulfate solution and water). The crude material (2.6 g) was chromatographed over silica gel (200 g) using the solvent system ethyl acetate:-benzene-1:3 to obtain 1.32 g of the title compound.

(C)
(3S)-1-[N-[3-[[(t-Butyloxy)carbonyl]amino]-2-hydroxy-4-phenylbutyl]-N-[(phenylmethoxy)carbonyl]-L-alanyl]-L-proline, t-butyl ester (3S)-1-[N-[3-[[(t-Butyloxy)carbonyl]amino]-2-oxo-4-phenylbutyl]-N-[(phenylmethoxy)carbonyl]-L-alanyl]-L-proline, t-butyl ester (1.75 g, 2.75 mmol) was dissolved in ethanol (15 ml), and stirred in an ice bath. Sodium borohydride (150 mg, 3.95 mmol) was added and the solution was stirred at room temperature for 90 minutes. It was then evaporated, taken into ethyl acetate and washed with 10% aqueous potassium hydrogen sulfate solution. The ethyl acetate solution after evaporation was chromatographed over silica gel (100 g)

using the solvent system ethyl acetate:hexane-4:6 to obtain 1.1 g of the title compound.

(D)

(3S)-1-[N-[3-[[(t-Butyloxy)carbonyl]amino]-2-hydroxy-4-phenylbutyl]-L-alanyl-L-proline, t-butyl ester, hydrochloride (3S)-1-[N-[3-[[(t-Butyloxy)carbonyl]amino]-2-hydroxy-4-phenylbutyl]-N-[(phenylmethoxy)carbonyl]-L-alanyl]-L-proline, t-butyl ester (550 mg, 0.86 mmol) was dissolved in methanol (35 ml) and hydrochloric acid (1N, 0.86 ml). Palladium on carbon catalyst (10%, 200 mg) was added and the solution was stirred under an atmosphere of hydrogen overnight, filtered through Hyflo and evaporated yielding 450 mg of the title compound.

(E)

(3S)-1-[N-(3-Amino-2-hydroxy-4-phenylbutyl)-L-alanyl]-L-proline, trifluoroacetate salt (1:2)

(3S)-1-[N-[3-[[(t-Butyloxy)carbonyl]amino]-2-hydroxy-4-phenylbutyl]-L-alanyl-L-proline, t-butyl ester, hydrochloride (400 mg, 0.74 mmol) was dissolved in trifluoroacetic acid (4 ml) and anisole (0.4 ml, 3.7 mmol). After maintaining the solution at room temperature for 75 minutes, it was evaporated and reevaporated from benzene and ether. The residue was then redissolved in water and lyophilized yielding 404 mg of the title compound, melting point 71°–83° C.

Analysis Calc'd. for $C_{18}H_{27}N_3O_4.2C_2HF_3O_2.1.23M-H_2O$: C, 44.07; H, 5.29; N, 7.01; F, 19.01 Found: C, 44.07; H, 4.99; N, 7.00; F, 18.8

EXAMPLE 5

N-[N-[N-[(2±,3S)-3-Amino-2-hydroxy-5-methylhexyl]-L-leucyl]-L-valyl]-L-phenylalanine, methyl ester, dihydrochloride (A) [(Phenylmethoxy)carbonyl]-L-leucine chloromethyl ketone A mixed carbonic anhydride of [(phenylmethoxy)carbonyl]-L-leucine was prepared as follows. A solution of 3.40 g (12.8 mmol) of [(phenylmethoxy)carbonyl]-L-leucine in 30 ml of dry tetrahydrofuran under argon was cooled to −15° C. and treated with 1.29 g (12.8 mmol) of N-methylmorpholine followed by 1.75 g (12.8 mmol) of isobutylchloroformate added dropwise while keeping the temperature between −10° and −15° C. Upon completion of the dropwise addition, the reaction was kept at −15° C. for 20 minutes, then rapidly filtered into a 500 ml filter flask containing ethereal diazomethane prepared from 5.71 g (38.8 mmol) of N-methyl-N'-nitro-N-nitrosoguanidine at −10° C. The resulting mixture was allowed to warm to 0° C. over a period of 1 hour, then stoppered with a balloon for gas evolution and refrigerated overnight. The light yellow solution was transferred to a 500 ml separatory funnel with 50 ml of ether rinse and the organic solution was shaken with 30 ml of 0.1 N aqueous acetic acid, water, saturated aqueous sodium bicarbonate and brine, dried (magnesium sulfate) and concentrated in vacuo to 4.00 g of yellow oil. This crude diazomethyl ketone was dissolved in 60 ml of ethyl acetate. The ethyl acetate solution was saturated with dry, gaseous hydrogen chloride at room temperature (immediate decolorization occurs), then stoppered and kept at room temperature for 15 minutes. The reaction mixture was then degassed with a stream of nitrogen, concentrated in vacuo to 4 g of oil and flash chromatographed on 150 g of LPS-1 silica gel eluted with 6:1, hexane:ether. Pooling of the product containing fractions yielded 3.36 g of the title compound isolated as a light yellow oil which would solidify upon freezer storage.

(B)

N-[N-[N-[(3S)-3-[[(Phenylmethoxy)carbonyl]amino]-2-oxo-5-methylhexyl]-L-leucyl]-L-valyl]-L-phenylalanine, methyl ester A mixture of 428 mg (1 mmol) of L-leucyl-L-valyl-L-phenylalanine, methyl ester, hydrochloride, 150 mg (1 mmol) of sodium iodide and 19 mg (0.1 mmol) of sodium bisulfite (on the basis of this experiment, its use was abandoned in the preparation of other compounds) was treated with 1 ml of dry dimethylformamide under argon at room temperature. Solid sodium bicarbonate (176 mg, 2.1 mmol) was added followed by a solution of 298 mg (1 mmol) of [(phenylmethoxy)carbonyl]-L-leucine chloromethyl ketone in 1 ml of dimethylformamide. After stirring for 24 hours at room temperature, the reaction was diluted with 50 ml of ethyl acetate and rinsed with two 10 ml portions of water, 10 ml of dilute aqueous sodium bisulfite, two 10 ml portions of water and brine, dried (magnesium sulfate) and concentrated in vacuo to 580 mg of crude product. Flash chromatography on 40 g of LPS-1 silica gel using 5:1, petroleum ether:acetone yielded 263 mg of the title compound as an oil.

(C)

N-[N-[N-[(2±,3S)-3-[[(Phenylmethoxy)carbonyl]amino-2-hydroxy-5-methylhexyl]-L-leucyl]-L-valyl]L-phenylalanine, methyl ester A solution of 569 mg (0.872 mmol) of N-[N-[N-[(3S)-3-[[(phenylmethoxy)carbonyl]amino]-2-oxo-5-methylhexyl]-L-leucyl]-L-valyl]-L-phenylalanine, methyl ester in 8 ml of methanol was cooled in an ice-water bath under argon and treated with 33 mg (0.872 mmol) of sodium borohydride. After 20 minutes, the reaction was quenched with 2 ml of water and extracted with 50 ml of ethyl acetate after adding an additional 15 ml of water. The aqueous layer was re-extracted with 25 ml of ethyl acetate and the combined organic extract was rinsed with two 10 ml portions of saturated aqueous sodium bicarbonate, 10 ml of water and brine, dried (magnesium sulfate) and concentrated in vacuo to 612 mg of crude product. Flash chromatography on 25 g of LPS-1 silica gel with 70:1, chloroform: methanol yielded 424 mg of product. This material was triturated with hexanes/chloroform, then re-evaporated to yield 369 mg of a white solid, melting point 55°–65° C.

(D)

N-[N-[N-[(2±,3S)-3-Amino-2-hydroxy-5-methylhexyl]-L-leucyl]-L-valyl]-L-phenylalanine, methyl ester, dihydrochloride A solution of 220 mg (0.336 mmol) of N-[N-[N-[(2±,3S)-3-[[(phenylmethoxy)carbonyl]-amino-2-hydroxy-5-methylhexyl]-L-leucyl]-L-valyl]-L-phenylalanine, methyl ester in 15 ml of methanol containing 1.01 ml of 1N aqueous hydrogen chloride was treated with 75 mg of 10% palladium on charcoal and subjected to a steady flow of hydrogen for 5¼ hours. The reaction was then filtered over Celite and concentrated in vacuo to yield 291 mg of crude product. This material was chromatographed on a 15×350mm LH-20 column run in methanol taking 3 ml fractions at a flow rate of 0.5 ml/minute. The product containing fractions were pooled to afford 185 mg of the title compound isolated as a hydrate with 0.9 mole of water, melting point 223°-238° C.

Analysis Calc'd. for $C_{28}H_{48}N_4O_5.2HCl.0.9H_2O$: C, 55.14; H, 8.23; N, 9.19; Cl, 11.63. Found: C, 55.11; H, 8.49; N, 9.13; Cl, 11.46.

EXAMPLE 6

N-[N-[N-[(3S)-3-Amino-2-hydroxy-5-methylhexyl]-L-leucyl]-L-valyl]-L-phenylalanine, methyl ester, dihydrochloride (faster isomer)

(A) [(t-Butyloxy)carbonyl]-L-leucine chloromethyl ketone

A solution of 19.2 g (77 mmol) of [(t-butyloxy)carbonyl]-L-leucine hydrate in 180 ml of dry tetrahydrofuran was cooled to −10° to −15° C. under an atmosphere of argon. The reaction mixture was treated with 7.79 g (77 mmol) of N-methyl-morpholine, added neat, followed by the careful addition of 10.5 g (77 mmol) of isobutylchloroformate, added neat and dropwise while keeping the internal temperature between −10° and −15° C. Upon completion of the addition, the solution was kept at −15° C. for 15 minutes.

Ethereal diazomethane, prepared from 24.2 g (165 mmol) of N-methyl-N'-nitro-N-nitrosoguanidine, was quickly dried over solid potassium hydroxide, then decanted into a 1 L filtering flask fitted with an argon sidearm connection, magnetically stirred and cooled in a −10° C. bath; total volume was ca. 400 ml. A filtering funnel was put in place and with vacuum momentarily connected at the sidearm, the mixed anhydride preparation was quickly filtered directly into the −10° C. ethereal diazomethane. Ether rinses were used to finish the transfer. The vacuum was replaced by the argon line and the reaction was allowed to warm to 0° C. and kept at that temperature for 1 hour. The flask was then stoppered well, fitted with a balloon and refrigerated overnight.

The reaction mixture was next rinsed with 400 ml each of 3% aqueous acetic acid, water, saturated sodium bicarbonate, water and brine, dried (magnesium sulfate) and concentrated in vacuo. The crude product was recrystallized from ether-petroleum ether to afford 17.2 g of the desired diazoketone, melting point 87°-89° C.

The diazoketone was dissolved in 600 ml of ether, cooled in an ice-water bath under argon and gaseous hydrogen chloride was gently bubbled into the reaction mixture. Within 3 minutes, the solution was decolorized and the flask was then stoppered and kept cold for 45 minutes. The reaction mixture was next rinsed with three 150 ml portions of ice-cold water, brine, dried (magnesium sulfate) and concentrated in vacuo to 17.4 g of white solid. Recrystallization from ether-petroleum ether gave a total of 15.5 g of the title compound, melting point 64°-65° C.

(B)

N-[N-[N-[(3S)-3-[[(t-Butyloxy)carbonyl]amino]-2-oxo-5-methylhexyl]-L-leucyl]-L-valyl]-L-phenyl-alanine, methyl ester A mixture of 856 mg (2 mmol) of L-leucyl-L-valyl-L-phenylalanine, methyl ester, hydrochloride, 100 mg (0.668 mmol) of sodium iodide, and 352 mg (4.2 mmol) of sodium bicarbonate in 3 ml of dimethylformamide was treated with 580 mg (2.2 mmol) of [(t-butyloxy)carbonyl]-L-leucine chloromethyl ketone dissolved in 2 ml of dimethylformamide, and the reaction was stirred at room temperature under a flow of nitrogen overnight. The reaction was then diluted with a mixture of 80 ml of ethyl acetate and 20 ml of ether, then washed with 20 ml portions of water (2x), 5% aqueous sodium bisulfite, water (2x), brine, dried (magnesium sulfate), and concentrated in vacuo to afford 1.1 g of crude product. Flash chromatography on 30 g of LPS-1 silica gel eluting with a 5:1 mixture of petroleum ether:acetone afforded 680 mg of partially purified product. Recrystallization from acetone:petroleum ether afforded 490 mg of the title compound, melting point 127°-129° C.

(C)

N-[N-[N-[(3S)-3-[[(t-Butyloxy)carbonyl]amino]-2-hydroxy-5-methylhexyl]-L-leucyl]-L-valyl]-L-phenylalanine, methyl ester (faster isomer)

A solution of 300 mg (0.49 mmol) of N-[N-[N-[(3S)-3-[[(t-butyloxy)carbonyl]amino]-2-oxo-5-methylhexyl]-L-leucyl]-L-valyl]-L-phenylalanine, methyl ester in 12 ml of methanol was cooled in an ice bath under a flow of nitrogen, and then treated with 98 mg (2.6 mmol) of sodium borohydride. The reaction was stirred for five minutes at 0° C., then diluted with 30 ml of water, and extracted with 50 ml of ethyl acetate. The organic layer was separated and washed with 10 ml portions of water, saturated aqueous sodium bicarbonate, water, brine, dried (magnesium sulfate), and concentrated in vacuo to afford 277 mg of crude product. This was combined with 230 mg of crude product from another experiment, and the entire amount was flash chromatographed on 25 g of LPS-1 silica gel, and eluted with a mixture of 3:1 petroleum ether:acetone to afford a mixture of diastereomers which was directly rechromatographed on an identical size column of LPS-1 silica gel, and eluted with a 6:1 mixture of the same solvent system to yield 157 mg of the fast diastereomer, 87 mg of the slow diastereomer, and 212 mg of a mixture of diastereomers. The mixture fraction was rechromatographed on 16 g of LPS-1 silica gel, and eluted with a 6:1 ratio of the same solvent mixture to afford an additional 49 mg of the fast diastereomer, an additional 60 mg of the slow diastereomer, and an additional 87 mg of a mixed fraction. The mixed fraction was chromatographed on 8.7 g of LPS-1 silica gel, and eluted with an 8:1 ratio of the same solvent system. All fractions of the fast diastereomers from all columns were combined to yield 232 mg of an oil. The oil was dissolved in ~100 ml of ether, and upon concentration in vacuo, the oil . solidified to afford 225 mg of the title compound as a hydrate with 0.8 mole of water.

All of the fractions of the slower moving diastereomer from all of the columns were combined to afford 182 mg of solid as a 0.4 mole hydrate.

(D)

N-[N-[N-[(3S)-3-Amino-2-hydroxy-5-methylhexyl]-L-leucyl]-L-valyl]-L-phenylalanine, methyl ester, dihydrochloride (faster isomer)

A solution of 250 mg of N-[N-[N-[(3S)-3-[[(t-butyloxy)carbonyl]amino]-2-hydroxy-5-methylhexyl]-L-leucyl]-L-valyl]-L-phenylalanine, methyl ester (faster isomer) in 3 ml of ethyl acetate was cooled in an ice bath under nitrogen then treated with anhydrous hydrogen chloride gas to saturation. Once the reaction was saturated, the ice bath was removed, the reaction was stoppered, and stirred at ambient temperature. After one hour, the reaction was concentrated to dryness in vacuo, then recrystallized from methanol/ether at room temperature, and refrigerated overnight to afford 155 mg of the title compound as a hydrate with 1.0 mole of water, melting point 220°–223° C., dec.

Analysis Calc'd. for $C_{28}H_{48}N_4O_5 \cdot 2HCl \cdot 1.0MH_2O$: C, 54.98; H, 8.57; N, 9.16; Cl, 11.59. Found: C, 55.05; H, 8.50; N, 9.15; Cl, 11.51.

EXAMPLE 7

N-[N-[N-[(3S)-3-Amino-2-hydroxy-5-methylhexyl]-L-leucyl]-L-valyl]-L-phenylalanine, methyl ester, dihydrochloride (slower isomer)

A solution of 250 mg of N-[N-[N-[(3S)-3-[[(t-butyloxy)carbonyl]amino]-2-hydroxy-5-methylhexyl]-L-leucyl]-L-valyl]-L-phenylalanine, methyl ester (slower isomer) (see example 6C) in 3 ml of ethyl acetate and 1.5 ml of dichloromethane was cooled in an ice bath under nitrogen, and then treated with anhydrous hydrogen chloride gas to saturation. Once the reaction was saturated, the ice bath was removed, the reaction was stoppered, and stirred at ambient temperature. After one hour, the reaction was concentrated to dryness in vacuo, resuspended in 5 ml of ethyl acetate, cooled in an ice bath under nitrogen, resaturated with anhydrous hydrogen chloride and stoppered. After 30 minutes, the reaction was concentrated to dryness in vacuo, then recrystallized from methanol/ether at room temperature, and refrigerated overnight to afford 200 mg of the title compound as a hydrate with 0.4 mole of water, melting point 242°–252° C., dec.

Analysis Calc'd. for $C_{28}H_{48}N_4O_5 \cdot 2HCl \cdot 0.4MH_2O$: C, 55.96; H, 8.52; N, 9.33; Cl, 11.80. Found: C, 55.96; H, 8.42; N, 9.31; Cl, 11.70.

EXAMPLE 8

(3S)-N-[N-(3-Amino-2-hydroxy-5-methylhexyl)-L-leucyl]-L-valine, methyl ester, dihydrochloride (Isomer A)

(A) [(Phenylmethoxy)carbonyl]-L-leucine, 2-(trimethylsilyl)ethyl ester

A mixture of 20.1 g (75.7 mmol) of [(phenylmethoxy)-carbonyl]-L-leucine, 0.925 g (7.57 mmol) of dimethylaminopyridine and 8.95 g (75.7 mmol) of 2-trimethylsilylethanol in 200 ml of dichloromethane was cooled in an ice bath under nitrogen and treated with a solution of 15.6 g (75.7 mmol) of dicyclohexylcarbodiimide in 50 ml of dichloromethane. The ice bath was removed after 30 minutes and the reaction allowed to come to room temperature overnight. The reaction mixture was filtered, concentrated in vacuo and partitioned between 800 ml of ether and 200 ml of water. The organic layer was separated and further rinsed with saturated sodium bicarbonate, water, 10% potassium bisulfate, water and brine, then dried (magnesium sulfate) and concentrated in vacuo to 26.1 g of crude product. Flash filtration over silica gel (180 g in 20:1, hexanes:ethyl acetate) yielded 22.9 g of crude product which was chromatographed using a Waters Prep 500 LC, two columns eluted with 15:1, hexanes:ethyl acetate (250 ml/minute, 200 ml fractions). Combining the pure fractions yielded 19.6 g of the title compound as an oil: $[\alpha]_D = 7.3°$ (c=1, chloroform).

(B) L-Leucine, 2-(trimethylsilyl)ethyl ester

To a solution of 9.1 g (24.9 mmol) of [(phenylmethoxy)carbonyl]-L-leucine, 2-(trimethylsilyl)ethyl ester in 200 ml of ethyl acetate cooled in an ice bath under nitrogen was added 1 g of 10% palladium on charcoal. The reaction mixture was subjected to a steady stream of hydrogen for 2½ hours at room temperature, then filtered and concentrated in vacuo to remove volatiles. The liquid product obtained was homogeneous by TLC. The yield was 5.8 g and the free amino-ester was used directly without further characterization.

(C) N-[(3S)-3-[[(t-Butyloxy)carbonyl]amino]-2-oxo-5-methylhexyl]-L-leucine, 2-(trimethylsilyl)ethyl ester To a mixture of 5.47 g (23.6 mmol) of L-leucine, 2-(trimethylsilyl)ethyl ester, 1.06 g (7.1 mmol) of sodium iodide, and 2.0 g (23.6 mmol) of sodium bicarbonate in 18 ml of dimethylformamide was added, in one portion, a solution of 3.55 g (13.5 mmol) of [(t-butyloxy)carbonyl]-L-leucine chloromethyl ketone (see example 6A) in 18 ml of dimethylformamide. The reaction, under an atmosphere of nitrogen, was stirred at ambient temperature overnight, then diluted with 500 ml of 1:1, ethyl acetate:ether and washed with 100 ml portions of water, 5% sodium bisulfite, water and brine, then dried (magnesium sulfate) and concentrated in vacuo to 7.8 g of crude product.

Flash chromatography on 85 g of LPS-1 silica gel eluted with 10:1, hexanes:ethyl acetate yielded 5.0 g of the title compound isolated as an oil: $[\alpha]_D = -15.5°$ (c=1, chloroform).

(D) N-[(3S)-3-[[(t-Butyloxy)carbonyl]amino]-2-hydroxy-5-methylhexyl]-L-leucine, 2-(trimethylsilyl)ethyl ester To a solution of 5.0 g (10.9 mmol) of N-[(3S)-3-[[(t-butyloxy)carbonyl]amino]-2-oxo-5-methylhexyl]-L-leucine, 2-(trimethylsilyl)ethyl ester in a mixture of 150 ml of tetrahydrofuran and 50 ml of water cooled in an ice-water bath was added 2.1 g (54.5 mmol) of sodium borohydride. After 5 minutes, the reaction was poured into 300 ml of water and extracted with 600 ml of ethyl acetate. The organic extract was rinsed further with water and brine, dried (magnesium sulfate) and concentrated in vacuo to yield 4.7 g of crude product. Flash chromatography on 140 g of LPS-1 silica gel eluted with 10:1, petroleum ether:acetone yielded 3.5 g of the title compound as an oil. By $^{13}C$-NMR analysis, material prepared in this manner is essentially a 1:1 mixture of diastereomers.

(E) N-[(3S)-3-[[(t-Butyloxy)carbonyl]amino]-2-hydroxy-5-methylhexyl]-N-[(phenylmethoxy)carbonyl]-L-leucine, 2-(trimethylsilyl)ethyl ester (2 isomers)

A mixture of 3.5 g (7.6 mmol) of N-[(3S)-3-[[(t-butyloxy)carbonyl]amino]-2-hydroxy-5-methylhexyl]-L-leucine, 2-(trimethylsilyl)ethyl ester and 2.8 g (11.4 mmol) of N-[[(phenylmethoxy)carbonyl]oxy]succinimide in 13.5 ml of dry tetrahydrofuran was stirred under nitrogen in a stoppered flask at ambient temperature for 48 hours, then diluted with 100 ml of ether and rinsed with water and brine, dried (magnesium sulfate) and concentrated in vacuo to 5.6 g of crude product. The mixture was flash filtered through 60 g of LPS-1 silica gel eluted with 20:1, petroleum ether:acetone then separated on a Waters Prep 500 LC using two columns eluted with 25:1, petroleum ether:acetone (250 ml/minute, 200 ml fractions).

Homogeneous fractions of the first isomer eluted were pooled to afford 1.53 g of "fast" isomer (Isomer B): $[\alpha]_D = -57.4°$ (c=1, chloroform); TLC $R_f=0.24$, silica gel in 10:1, petroleum ether:acetone.

After collecting 132 mg of a mixture fraction, pure "slow" isomer (Isomer A) was obtained as an oil, weighing 1.72 g: $[\alpha]_D = -25\ 2°$ C. (c=1, chloroform); TLC $R_f=0.21$, silica gel in 10:1, petroleum ether:acetone.

(F)

N-[[(4S)-3-[(t-Butyloxy)carbonyl]-2,2-dimethyl-4-(2-methylpropyl)-5-oxazolidinyl]methyl]-N-[(phenylmethoxy)carbonyl]-L-leucine, 2-(trimethylsilyl)ethyl ester (Isomer A)

N-[(3S)-3-[[(t-Butyloxy)carbonyl]amino]-2-hydroxy-5-methylhexyl]-N-[(phenylmethoxy)carbonyl]-L-leucine, 2-trimethylsilyl)ethyl ester (Isomer A) (2.42 g, 4.1 mmol) was dissolved in 72 ml of dry dichloromethane and treated with 5.9 g (82 mmol) of 2-methoxypropene, followed by 0.206 g (0.82 mmol) of pyridinium-p-toluenesulfonic acid. The reaction was stirred at room temperature under nitrogen for one hour then diluted with 500 ml of ether and rinsed with water and brine, dried (magnesium sulfate) and concentrated in vacuo to 3.1 g of crude product. Chromatography on a Waters Prep 500 LC using two columns eluted with 35:1, petroleum ether:acetone (250 ml/minute, 125 ml fractions) yielded 2.2 g of the title compound as an oil: $[\alpha]_D = -4.3°$ C. (c=1, chloroform); TLC $R_f=0.44$, silica gel in 15:1, petroleum ether:acetone.

(G)

N-[N-[[(4S)-3-[(t-Butyloxy)carbonyl]-2,2-dimethyl-4-(2-methylpropyl)-5-oxazolidinyl]methyl]-N-[(phenylmethoxy)carbonyl]-L-leucyl]-L-valine, methyl ester (Isomer A)

To a solution of 2.2 g (3.46 mmol) of N-[[(4S)-3-[(t-butyloxy)carbonyl]-2,2-dimethyl-4-(2-methylpropyl)-5-oxazolidinyl]methyl]-N-[(phenylmethoxy)carbonyl]-L-leucine, 2-(trimethylsilyl)ethyl ester (Isomer A) in 26 ml of dimethylformamide under nitrogen at room temperature was added 2.2 g (6.92 mmol) of tetrabutylammonium fluoride, trihydrate. After 15 minutes, the reaction was diluted with 200 ml of 1:1, ether: ethyl acetate and rinsed with three 75 ml portions of water, brine and dried (magnesium sulfate). Removal of solvents in vacuo afforded 1.85 g of the carboxylic acid analog of the starting ester, one spot by TLC, $R_f=0.64$ on silica gel in 20:1:1, chloroform:methanol:acetic acid.

The entire crude carboxylic acid product was dissolved in 30 ml of tetrahydrofuran under nitrogen. The solution was cooled in an ice bath and treated with 580 mg (3.46 mmol) of L-valine, methyl ester, hydrochloride, 530 mg (3.46 mmol) of hydrated hydroxybenzotriazole, and 749 mg (3.63 mmol) of dicyclohexylcarbodiimide followed by 350 mg (3.46 mmol) of N-methylmorpholine. The reaction mixture was allowed to warm to room temperature overnight, then filtered and taken up in 200 ml of 1:1, ethyl acetate:ether. The organic solution was rinsed with 60 ml portions of 5% potassium bisulfate, water, saturated sodium bicarbonate, water and brine, dried (magnesium sulfate) and concentrated in vacuo to 2.4 g of crude product. Flash chromatography on 120 g of LPS-1 silica gel eluted with 20:1, petroleum ether:acetone afforded 1.9 g of the title compound, $[\alpha]_D = +10.4°$ (c=1, chloroform); TLC $R_f=0.08$, silica gel in 15:1, petroleum ether:acetone.

(H)

(3S)-N-[N-(3-Amino-2-hydroxy-5-methylhexyl)-N-[(phenylmethoxy)carbonyl]-L-leucyl]-L-valine, methyl ester (Isomer A)

A solution of 177 mg (nom. 0.27 mmol) of N-[N-[[(4S)-3-[(t-butyloxy)carbonyl]-2,2-dimethyl-4-(2-methylpropyl)-5-oxazolidinyl]methyl]-N-[(phenylmethoxy)carbonyl]-L-leucyl]-L-valine, methyl ester (Isomer A) in 1.7 ml of dry dichloromethane was cooled in an ice bath under nitrogen, then treated with 0.85 ml of distilled trifluoroacetic acid. After 1½ hours, the reaction was concentrated in vacuo to an oil, dissolved in 1 ml of distilled tetrahydrofuran, and treated with 0.6 ml (0.6 mmol) of 1N hydrochloric acid. After four hours, the reaction was worked up by treating with 6 ml of saturated sodium bicarbonate (aqueous), then extracting with 2×6 ml of chloroform, washing the organic extracts with brine, drying (magnesium sulfate), and concentrating to afford 127 mg of the title compound as a crude oil.

(I)

N-[N-[N-[(3S)-3-Amino-2-hydroxy-5-methylhexyl]-L-leucyl]-L-valyl]-L-phenylalanine, methyl ester, dihydrochloride (Isomer A)

A solution of 127 mg (nominally 0.25 mmol) of (3S)-N-[N-(3-amino-2-hydroxy-5-methylhexyl)-N-[(phenylmethoxy)carbonyl]-L-leucyl]-L-valine, methyl ester (Isomer A) in 3 ml of methanol was treated with 0.75 ml (0.75 mmol) of 1N hydrochloric acid and 75 mg of 10% palladium on charcoal and subjected to a steady stream of hydrogen at atmospheric pressure. After 3½ hours, a silica gel TLC run in 9:1, chloroform:methanol, checked with UV and vanillin, indicated complete disappearance of the starting compound. The reaction was worked up by filtering through a Celite pad, concentrating the filtrate in vacuo, and recrystallizing the residue from methanol/ether at room temperature, then storing in a freezer overnight. The recrystallized yield was very low, so the crystals were recombined with the mother liquor, and the entire crude product was concentrated in vacuo to afford 77 mg of solid. Chromatography was performed on a 35 ml column of HP-20 resin, eluting with a gradient from 175 ml of 96:3:1 to 175 ml of 2:2:96, water:1N hydrogen chloride:methanol. The fractions were checked by silica gel TLC run in 5:1:1:1, butanol:pyridine: acetic acid:water, and sprayed with Rydons. Pooling of the product containing fractions followed by lyophilization afforded 77 mg of the title compound as a hydrate with 1.0 mole of water, melting point 136°-158° C.

Analysis Calc'd. for $C_{19}H_{39}N_3O_4 \cdot 2HCl \cdot 1.0H_2O$: C, 49.13; H, 9.33; N, 9.05; Cl, 15.27. Found: C, 49.11; H, 9.03; N, 9.04; Cl, 15.30.

EXAMPLE 9

(3S)-N-[N-(3-Amino-2-hydroxy-5-methylhexyl)-L-leucyl]-L-valine, methyl ester, dihydrochloride (Isomer B)

A solution of 109 mg of (3S)-N-[N-(3-amino-2-hydroxy-5-methylhexyl)-N-[(phenylmethoxy)-carbonyl]-L-leucyl]-L-valine, methyl ester (Isomer B, prepared from N-[(3S)-3-[[(t-butyloxy)carbonyl]-amino]-2-hydroxy-5-methylhexyl]-N-[(phenylmethoxy)carbonyl]-L-leucine, 2-(trimethylsilyl)ethyl ester, Isomer B using a procedure analogous to that described in Example 8 for preparing the corresponding Isomer A) in 3 ml of methanol was treated with 0.63 ml of 1N hydrochloric acid and 75 mg of 10% palladium on charcoal and subjected to a steady stream of hydrogen at 1 atmosphere pressure. After 3 hours, a silica gel TLC run in 9:1, chloroform: methanol, checked with UV and PMA, indicated complete disappearance of the starting compound. The reaction was worked up by filtering through a Celite pad, concentrating the filtrate in vacuo, and recrystallizing the residue from methanol/ether at room temperature, then storing in the freezer overnight to afford 73 mg of partially purified product, melting at 232°–234° C. Chromatography was performed on a 35 ml column of HP-20 resin, eluting with a gradient from 175 ml of 96:3:1 to 2:2:96, water: 1N hydrochloric acid: methanol. The fractions were checked by silica gel TLC run in 5:1:1:1, butanol: pyridine:acetic acid:water and sprayed with ninhydrin. Pooling of product containing fractions followed by lyophilization yielded 17 mg of the title compound as a hydrate with 1.0 mole of water, melting point 125°–140° C.

Analysis Calc'd. for $C_{19}H_{39}N_3O_4 \cdot 2HCl \cdot 1.0H_2O$: C, 49.13; H, 9.33; N, 9.05; Cl, 15.27 Found: C, 48.96; H, 8.99; N, 9.17; Cl, 14.95.

EXAMPLE 10

(3S)-N-[N-(3-Amino-2-hydroxy-4-phenylbutyl)-L-phenylalanyl]-L-leucine, dihydrochloride (A) (3S)-N-[N-[3-[[(t-Butyloxy)carbonyl]amino]-2-oxo-4-phenylbutyl]-L-phenylalanyl]-L-leucine, t-butyl ester To a stirred solution of L-phenylalanyl-L-leucine, t-butyl ester (4.13 g, 12 mmol) in 60 ml of dimethylformamide under argon was added N-[(t-butyloxy)carbonyl]-L-phenylalanine chloromethyl ketone (3.57 g, 12 mmol, see example 4A), sodium bicarbonate (1.01 g, 12 mmol) and sodium iodide (900 mg, 6 mmol, 0.5 equiv.). The reaction mixture was allowed to stir overnight, then the solvent was evaporated (<25° C., vacuum pump). The residue was taken up into ethyl acetate (300 ml) and washed with water (3×40 ml) and brine (40 ml), then dried (sodium sulfate) and evaporated to give 6.63 g of a yellow oil. This oil was purified by flash chromatography on 450 g of Merck silica gel (230–400 mesh), eluting with 3:1 hexane-ethyl acetate, to yield 5.05 g of the title compound as a light yellow solid. A portion was recrystallized from ethyl acetate-hexane to give a white solid, melting point 85°–87° C.

(B) (3S)-N-[N-[3-[[(t-Butyloxy)carbonyl]amino]-2-hydroxy-4-phenylbutyl]-L-phenylalanyl]-L-leucine, t-butyl ester A solution of (3S)-N-[N-[3-[[(t-butyloxy)carbonyl]amino]-2-oxo-4-phenylbutyl]-L-phenylalanyl]-L-leucine, t-butyl ester (1.46 g, 2.45 mmol) in 15 ml of methanol was cooled to 0° C. Sodium borohydride (93 mg, 2.45 mmol) was added in portions over 5 minutes. After 15 minutes, the solvent was evaporated. The residue was taken up into ethyl acetate (100 ml), washed with water, dried (sodium sulfate) and evaporated to give 1.14 g of a slightly yellow gum. This material was combined with 1.73 g of material similarly prepared. The combined material (2.87 g) was purified by flash chromatography on 215 g of Merck silica gel (230–400 mesh), eluting with hexane-ethyl acetate (1.5:1), to give 2.11 g of the title compound as a colorless oil; TLC: $R_f=0.19$, 1.25:1 hexane-ethyl acetate.

(C) (3S)-N-[N-(3-Amino-2-hydroxy-4-phenylbutyl)-L-phenylalanyl]-L-leucine, dihydrochloride A solution of (3S)-N-[N-[3-[[(t-butyloxy)carbonyl]amino]-2-hydroxy-4-phenylbutyl]-L-phenylalanyl]-L-leucine, t-butyl ester (2.00 g, 3.34 mmol) in 50 ml of 1.3N hydrogen chloride in acetic acid was allowed to stir for 2 hours at room temperature. The solvent was evaporated (<25° C., vacuum pump) and the residue was triturated with ether to give 1.73 g of a white solid. Analysis by $^{13}$C-NMR revealed unreacted t-butyl ester; therefore, the solid and the ether filtrate were recombined, concentrated in vacuo, and treated once more with 35 ml of 1.3N hydrogen chloride in acetic acid. After 15 hours, the solvent was evaporated and the residue was triturated with ether to give 1.49 g of a white solid. Purification by chromatography on HP-20, eluting with 0–20% acetonitrile in 0.01N hydrochloric acid yielded 1.46 g of the title compound as a white solid, melting point 180°–201° C. (sinters>145° C.).

Analysis Calc'd. for $C_{25}H_{35}N_3O_4 \cdot 2HCl \cdot 1.0H_2O$: C, 56.39; H, 7.38; N, 7.89; Cl, 13.32 Found: C, 56.54; H, 7.43; N, 7.83; Cl, 13.43.

EXAMPLE 11

N-[N-[(3S)-3-Amino-2-hydroxy-5-methylhexyl]-L-phenylalanyl]-L-leucine, hydrochloride salt (1:2)

(A) N-[N-[(3S)-3-[[(t-Butyloxy)carbonyl]amino]-2-oxo-5-methylhexyl]-L-phenylalanyl]-L-leucine, t-butyl ester L-Phenylalanyl-L-leucine, t-butyl ester hydrochloride (2.22 g, 6 mmol) was partitioned between saturated sodium bicarbonate (60 ml) and ethyl acetate (90 ml). The ethyl acetate layer was washed with saturated sodium bicarbonate (20 ml), water (2×20 ml) and brine (2×20 ml), then dried (sodium sulfate) and evaporated to give L-phenylalanyl-L-leucine, t-butyl ester (2.07 g) as a colorless oil.

To a stirred solution of L-phenylalanyl-L-leucine, t-butyl ester (6 mmol) in 30 ml of dimethylformamide under argon was added N-[(t-butyloxy)carbonyl]-L-leucine chloromethyl ketone (1.58 g, 6 mmol), sodium bicarbonate (505 mg, 6 mmol) and sodium iodide (450 mg, 3 mmol, 0.5 equiv.). The reaction mixture was allowed to stir for 14 hours and the solvent was then evaporated (<25° C., vacuum pump). The residue was taken up into 150 ml of ethyl acetate and washed with water (3×30 ml) and brine (2×30 ml), then dried (sodium sulfate) and evaporated to give 3.57 g of a pale yellow gum. Purification by flash chromatography on Merck silica gel, eluting with 3:1 hexane-ethyl acetate, afforded 2.77 g of the title compound as a colorless oil; TLC: $R_f=0.24$, 3:1 hexane-ethyl acetate.

(B) N-[N-[(3S)-3-[[(t-Butyloxy)carbonyl]amino]-2-hydroxy-5-methylhexyl]-L-phenylalanyl]-L-leucine, t-butyl ester A solution of N-[N-[(3S)-3-[[(t-butyloxy)carbonyl]amino]-2-oxo-5-methylhexyl]-L-phenylalanyl]-L-leucine, t-butyl ester (2.66 g, 4.74 mmol) in 25 ml of methanol was cooled to 0° C. Sodium borohydride (195 mg, 5.15 mmol) was added in five portions over approximately 1.5 minutes. After 20 minutes, the solvent was evaporated. The residue was taken up into 150 ml of ethyl acetate, washed with water (4×30 ml) and brine, dried (sodium sulfate) and evaporated to give 2.49 g of a colorless oil. This oil was purified by flash chromatography on silica gel, with hexane-ethyl acetate (1.5:1) as the eluent, to yield 2.35 g of the title compound as a white foam; TLC: $R_f$=0.11, 0.17 (diastereomers, 9:1 toluene-acetone.

(C)

N-[N-[(3S)-3-Amino-2-hydroxy-5-methylhexyl]-L-phenylalanyl]-L-leucine, hydrochloride salt (1:2)

A solution of N-[N-[(3S)-3-[[(t-butyloxy)carbonyl]amino]-2-hydroxy-5-methylhexyl]-L-phenylalanyl-L-leucine, t-butyl ester (845 mg, 1.5 mmol) in 22 ml of 1.3N hydrogen chloride in acetic acid was allowed to stir at room temperature for 2 hours. The resultant thick white slurry was evaporated to dryness in vacuo. The residue was dissolved in water and the solution was microfiltered and concentrated in vacuo to give a white gummy residue. Trituration with ether afforded 698 mg of the title compound as a fine white powder, melting point 179°–203° C. (with decomposition). The 13C-NMR spectrum was consistent with an approximately 2:1 mixture of alcohol isomers.

EXAMPLE 12

N-[(2R,3S)-3-Amino-2-hydroxy-5-methylhexyl]-L-leucinamide, dihydrochloride (A)

N-[[(4S)-3-[(t-Butyloxy)carbonyl]-2,2-dimethyl-4-(2-methylpropyl)-5-oxazolidinyl]methyl]-N-[(phenylmethoxy)carbonyl]-L-leucinamide A solution of N-[[(4S)-3-[(t-butyloxy)carbonyl]-2,2-dimethyl-4-(2-methylpropyl)-5-oxazolidinyl]methyl]-N-[(phenylmethoxy)carbonyl]-L-leucine, 2-(trimethylsilyl)ethyl ester (1.3 g, 2.05 mmol; see example 8F) in 17 ml of dimethylformamide was treated with 678 mg (2.15 mmol) of tetrabutylammonium fluoride trihydrate, and the reaction was stirred at ambient temperature for 90 minutes. The reaction was cooled to −20° C. under nitrogen, treated with 279 μl (2.15 mM) of isobutyl chloroformate, and maintained at −15° C. for 15 minutes. It was treated with 1.1 ml (6.60 mM) of 6N ammonia/methanol, maintained at 0° C. for several minutes, and then allowed to warm to ambient temperature. After one hour, the reaction was worked up by treatment with 150 ml of water, extracting with 3-300 ml of a 1:1 mixture of ethyl acetate:ether, drying, and concentrating in vacuo to afford 1.1 g of crude product. The compound was flash chromatographed on 110 g of silica gel with 5% acetone in petroleum ether to separate out the starting material, and eluted with 10% acetone in petroleum ether to obtain the product. The product containing fractions were pooled to afford 635 mg of the title compound [α]$_D$= +4.9° (c=1, chloroform); silica gel TLC $R_f$=0.65 in 1:1, petroleum ether-:acetone.

Analysis Calc'd. for C$_{29}$H$_{47}$N$_3$O$_6$ (533.7): C, 65.26; H, 8.88; N, 7.87 Found: C, 65.10; H, 8.87; N, 7.63

(B)

N-[(2R,3S)-3-Amino-2-hydroxy-5-methylhexyl]-L-leucinamide, dihydrochloride

A solution of 250 mg (0.47 mmol) of N-[[(4S)-3-[(t-butyloxy)carbonyl]-2,2-dimethyl-4-(2-methylpropyl)-5-oxazolidinyl]methyl]-N-[(phenylmethoxy)carbonyl]-L-leucinamide in 3 ml of dry dichloromethane was cooled in an ice bath under nitrogen, and treated with 1.5 ml of distilled trifluoroacetic acid. The reaction was stirred at ambient temperature. After 1 hour, the solvent was removed in vacuo, the residue dissolved in 1.7 ml of distilled tetrahydrofuran, treated with 1.0 ml (1 mmol) of 1N hydrochloric acid, and stirred at ambient temperature. After three hours, the reaction was concentrated in vacuo, and the residue was stored in the freezer overnight. The next morning a solution of 259 mg of the free amine hydrochloride from above in 6 ml of a 3:1; acetic acid:water mixture was treated with 1.4 ml (1.4 mmol) of 1N hydrochloric acid, and 150 mg of 10% palladium on charcoal. It was reduced with a steady stream of hydrogen at 1 atmosphere pressure. After 4 hours, filtration of the reaction mixture followed by concentration of the filtrate afforded 242 mg of crude product. The compound was purified by chromatography on a 40 ml column of HP-20 resin, eluted with a gradient from 250 ml of 96:3:1 to 250 ml of 18:2:80, water:1N hydrochloric acid:methanol. The product containing fractions were pooled and concentrated in vacuo then lyophilized from water to obtain 112 mg of the title compound as a 1.3 mole water solvate.

Analysis Calc'd. for C$_{13}$H$_{29}$N$_3$O$_2$·2HCl·1.3H$_2$O: C, 43.89; H, 9.52; N, 11.81; Cl, 19.93. Found: C, 43.91; H, 9.46; N, 12.09; Cl, 19.93

What is claimed is:

1. A method of relieving pain in a mammalian host suffering therefrom, which comprises administering an effective amount of a compound having the formula

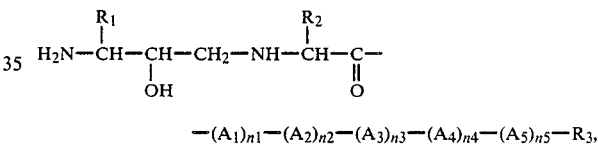

$$-(A_1)_{n1}-(A_2)_{n2}-(A_3)_{n3}-(A_4)_{n4}-(A_5)_{n5}-R_3,$$

or a pharmaceutically acceptable salt thereof, wherein
R$_1$ and R$_2$ are each independently hydrogen, alkyl, carboxyalkyl, halo substituted alkyl, hydroxyalkyl, aminoalkyl, mercaptoalkyl, alkylthioalkyl, (cycloalkyl)alkyl, (heteroaryl)alkyl, arylalkyl, carbamoylalkyl, guanidinylalkyl, or heteroaryl;

R$_3$ is hydroxy, alkoxy, (substituted alkyl)oxy, arylalkoxy, (heteroaryl)alkoxy or —NY$_1$Y$_2$, wherein Y$_1$ and Y$_2$ are each independently hydrogen, alkyl, aryl, or arylalkyl, or Y$_1$ is hydrogen and Y$_2$ is substituted alkyl or (heteroaryl)alkyl;

A$_1$ is glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, norvalyl, or

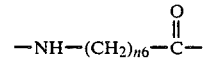

A$_2$, A$_3$, A$_4$ and A$_5$ each is independently glycyl, alanyl, leucyl, phenylalanyl, arginyl, sarcosyl, seryl, asparagyl, lysyl, glutamyl, histidyl, tryptophyl, cysteinyl, methionyl, threonyl, tyrosyl, leucyl, valyl, aspartyl, prolyl, norleucyl, or norvalyl; and n$_1$, n$_2$, n$_3$, n$_4$ and n$_5$ each is independently 0 or 1; and wherein the terms "alkyl" and "alkoxy" refer to straight and branched chain groups having 1 to 7 carbon atoms;

the term "halo substituted alkyl" refer to alkyl groups in which one, or more, hydrogens have been replaced by chloro, bromo, or fluoro groups;

the term "cycloalkyl" refers to cycloalkyl groups having 3, 4, 5, 6, or 7 carbon atoms;

the term "substituted alkyl" refers to alkyl groups substituted with one, or more, hydroxy or $-NY_3Y_4$ groups wherein $Y_3$ and $Y_4$ are the same or different and each is hydrogen or alkyl, $Y_3$ is hydrogen and $Y_4$ is aryl, or $Y_3$ and $Y_4$ together with the nitrogen atom to which they are attached form a heterocyclic group having the formula

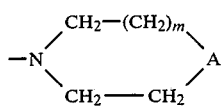

and A is CH—Q, oxygen, or N—Q, Q is hydrogen or alkyl and m is 0 or 1;

the term "heteroaryl" refers to 2- or 3-furanyl, 2- or 3-thienyl, 2-, 3- or 4-pyridinyl, 4-imidazolyl and 3-indolyl; and the term "aryl" refers to phenyl and phenyl substituted with 1, 2 or 3 alkyl, alkoxy, alkylthio, hydroxy, chlorine, bromine, fluorine, amino, alkylamino, dialkylamino, nitro or trifluoromethyl groups.

2. A method in accordance with claim 1 wherein the compound has the formula

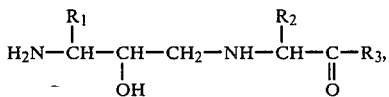

or a pharmaceutically acceptable salt thereof.

3. A method in accordance with claim 1 wherein the compound has the formula

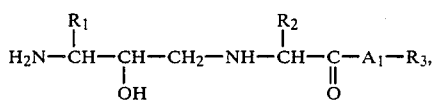

or a pharmaceutically acceptable salt thereof.

4. A method in accordance with claim 1 wherein the compound has the formula

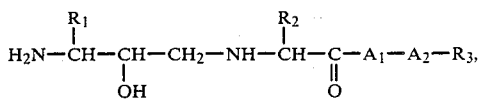

or a pharmaceutically acceptable salt thereof.

5. A method in accordance with claim 1 wherein the compound has the formula

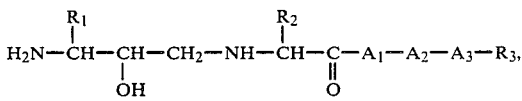

or a pharmaceutically acceptable salt thereof.

6. A method in accordance with claim 1 wherein the compound has the formula

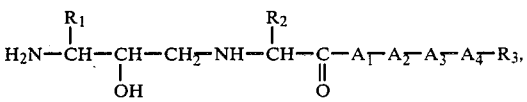

or a pharmaceutically acceptable salt thereof.

7. A method in accordance with claim 1 wherein the compound has the formula

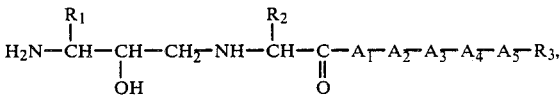

or a pharmaceutically acceptable salt thereof.

8. A method in accordance with claim 1 wherein one of $R_1$ and $R_2$ is phenylmethyl and the other is methyl.

9. A method in accordance with claim 1 wherein each of $R_1$ and $R_2$ is phenylmethyl.

10. A method in accordance with claim 1 wherein each of $R_1$ and $R_2$ is isobutyl.

11. A method in accordance with claim 1 wherein one of $R_1$ and $R_2$ is phenylmethyl and the other is isobutyl.

12. A method in accordance with claim 1 wherein $R_3$ is hydroxy.

13. A method in accordance with claim 1 wherein $R_3$ is alkoxy.

14. A method in accordance with claim 1 wherein $R_3$ is arylalkoxy.

15. A method in accordance with claim 1 wherein $R_3$ is $NY_1Y_2$.

* * * * *

UNITED STATES PATENT AND TRADEMARK OFFICE
CERTIFICATE OF CORRECTION

PATENT NO. : 4,552,866

DATED : November 12, 1985

INVENTOR(S) : Norma G. Delaney et al.

It is certified that error appears in the above—identified patent and that said Letters Patent is hereby corrected as shown below:

Column 21, line 48, "3-300" should be -- 3 x 300 --.

Column 22, line 59, after structural formula, add -- wherein $n_6$ is an integer of 2 to 15; --.

Signed and Sealed this

Eighteenth Day of March 1986

[SEAL]

Attest:

DONALD J. QUIGG

Attesting Officer

Commissioner of Patents and Trademarks